(12) United States Patent
Liu et al.

(10) Patent No.: US 8,181,525 B2
(45) Date of Patent: May 22, 2012

(54) UNIVERSAL ACOUSTIC EMISSION TEST SENSOR FIXING DEVICE

(75) Inventors: Jianfeng Liu, Chengdu (CN); Heping Xie, Chengdu (CN); Jin Xu, Chengdu (CN)

(73) Assignee: Sichuan University, Chengdu, Sichuan Province (CN)

( * ) Notice: Subject to any disclaimer, the term of this patent is extended or adjusted under 35 U.S.C. 154(b) by 306 days.

(21) Appl. No.: 12/689,785

(22) Filed: Jan. 19, 2010

(65) Prior Publication Data

US 2010/0313661 A1   Dec. 16, 2010

(30) Foreign Application Priority Data

Jun. 15, 2009   (CN) .......................... 2009 1 0059593

(51) Int. Cl.
*G01N 29/14*   (2006.01)
(52) U.S. Cl. .......................................... 73/587; 73/594
(58) Field of Classification Search .................... 73/587, 73/594, 801

See application file for complete search history.

(56) References Cited

U.S. PATENT DOCUMENTS

| 5,065,630 | A | * | 11/1991 | Hadcock et al. | 73/802 |
| 5,798,457 | A | * | 8/1998 | Paulson | 73/587 |
| 5,837,882 | A | * | 11/1998 | Bacigalupo et al. | 73/7 |
| 6,170,334 | B1 | * | 1/2001 | Paulson | 73/587 |
| 6,874,220 | B1 | * | 4/2005 | Jones | 29/594 |
| 2010/0313662 | A1 | * | 12/2010 | Liu et al. | 73/587 |

FOREIGN PATENT DOCUMENTS

| EP | 000470654 | * | 2/1992 |
| JP | 2004205315 | * | 7/2004 |

* cited by examiner

*Primary Examiner* — J M Saint Surin
(74) *Attorney, Agent, or Firm* — Harrity & Harrity, LLP (57) ABSTRACT

A universal acoustic emission test sensor fixing device includes a radial positioning mechanism, supporting mechanisms, bases, acoustic emission test sensor mounting mechanisms, and parallelism adjusting members, in which the supporting mechanism includes a main supporting arm and an auxiliary supporting arm, with one end of the auxiliary supporting arm fixedly connected to or hinged with the main supporting arm and the other end being provided with a ball head, and a parallelism adjusting member mounting mechanism is provided at the joint of the main supporting arm and the auxiliary supporting arm, and the base is provided with a spherical hole.

14 Claims, 6 Drawing Sheets

UNIVERSAL ACOUSTIC EMISSION TEST SENSOR FIXING DEVICE

FIELD OF THE INVENTION

The present invention relates to an acoustic emission test sensor fixing device used in columnar test piece experiment and test of materials such as rock and concrete.

BACKGROUND OF THE INVENTION

In rock mechanical experiments, when acoustic emission features of rock damage process and etc. are tested, the acoustic emission test sensors currently used do not have specific fixing devices, and two fixing methods of winding with rubber belt and fastening with bungee are commonly adopted in current experiments and tests. Acoustic emission test sensors generally have a diameter within the range of 5 mm to 15 mm and need to couple tested members using media such as a gel, butter, vaseline and etc. as a coupler, which result in that the fixing methods of winding with rubber belt and fastening with bungee are unable to ensure fine parallelism between the end face of the acoustic emission test sensor and the coupling face of the tested member and the fine coupling between the end face of the acoustic emission test sensor and the tested member, especially, test pieces with irregular shapes make the fixing more difficult. Also, couplers such as butter, vaseline and etc. may easily result in the adhesion reduction or failure of the rubber belt, and the rubber belt may easily form great binding on the acoustic emission test sensor during radial swelling and deforming of the tested member, so that it undertakes increasing force and is even damaged to some extent; for the fixing method of fastening by bungee, although the bungee is elongated by pulling during radial swelling and deforming of tested member and may deform to some extent, this fixing method may easily cause the acoustic emission test sensor to tumble, and thus it is difficult to ensure fine contact between the acoustic emission test sensor and the tested member. In addition, the above mentioned two fixing methods need to be performed before test pre-adding and adjustment cannot be made during the test, and it is also difficult to accurately contraposition the acoustic emission test sensor. The above mentioned two fixing methods also have the following problems: (1) they can hardly ensure the consistency of force to the acoustic emission test sensor in the same batch of tested members and may easily form many pseudo signals, thus resulting in much difficulty to analysis and judgment of the test result; and (2) they cause the mounting of other deforming test sensors very inconvenient.

SUMMARY OF THE INVENTION

The present invention may provide a universal acoustic emission test sensor fixing device, to ensure fine contact between the acoustic emission test sensor and the tested members with different shapes (being regular and irregular), and improve test efficiency and the accuracy and the truthfulness of the testing.

The universal acoustic emission test sensor fixing device according to the present invention comprises a radial positioning mechanism, supporting mechanisms, bases, acoustic emission test sensor mounting mechanisms, and parallelism adjusting members, wherein the supporting mechanisms, the bases, the acoustic emission test sensor mounting mechanisms, and the parallelism adjusting members are all in two sets; the supporting mechanism includes a main supporting arm and an auxiliary supporting arm, with one end of the auxiliary supporting arm being fixedly connected to or hinged with the main supporting arm and the other end being provided with a ball head, and a parallelism adjusting member mounting mechanism is provided at the joint of the main supporting arm and the auxiliary supporting arm, and the base is provided with a spherical hole matching the ball head of the auxiliary supporting arm. The above assemblies or members are assembled as follows: the main supporting arms of two sets of supporting mechanisms are respectively connected to the two free ends of the radial positioning mechanism in the way that the auxiliary supporting arms of the two sets of supporting mechanisms are respectively located at the inner sides of the main supporting arms and are arranged axis symmetrically with respect to the central line of the radial positioning mechanism, and the ball heads of the two auxiliary supporting arms are respectively located within the spherical holes of the two bases to form universal revolute pairs, two sets of acoustic emission test sensor mounting mechanisms are respectively mounted at the two bases, and two sets of parallelism adjusting members are respectively mounted on the two main supporting arms via mounting mechanisms provided on the main supporting arms.

Exemplary structures of the above assemblies constituting the acoustic emission test sensor fixing device according to the present invention are described as follows:

1. The radial positioning mechanism includes two elastomers and one screw, and the two elastomers are respectively connected with rigid ends at respective one end, each of said rigid ends is provided with a screw hole matching the screw, and the screw forms screw pairs respectively with the screw holes in the two rigid ends; or the radial positioning mechanism only consists of elastomers.

2. The base is a rectangular or circular platform and is provided with a slot in the lower portion, and the spherical holes matching the ball heads of the auxiliary supporting arm are provided in the upper surface of the base; corresponding to the structure of the base, the acoustic emission test sensor mounting mechanism comprises a plugboard matching the slot in the base, an acoustic emission test sensor mounting member and an acoustic emission test sensor fixing member; the plugboard is provided with a plugboard fixing buckle or a plugboard fixing screw hole, and the plugboard is inserted into the slot of the base and fixed with the base via a bolt or the fixing buckle; the acoustic emission test sensor mounting member is a cylinder provided with a gap and is fixedly connected with or forms a one-piece structure with the plugboard, with its inner diameter matching the outer diameter of an acoustic emission test sensor (during implementation, cylinders with different inner diameters can be made according to the acoustic emission test sensor, to form a series of cylinders meeting the demands of testing); the acoustic emission test sensor fixing member consists of a circular elastic plate provided with a gap and a fastening screw or a fixing buckle, when the acoustic emission test sensor is mounted within the cylinder with a gap, the circular elastic plate with a gap is put around the gap section of the cylinder, and then the acoustic emission test sensor is fixed within the cylinder via a fastening screw or the fixing buckle.

3. The base is a rectangular or circular platform and is provided with a connecting screw hole in the lower portion, and the spherical holes matching the ball heads of the auxiliary supporting arm are provided in the upper surface of the base; corresponding to the structure of the base, the acoustic emission test sensor mounting mechanism comprises a threaded section matching the connecting screw hole in the base, an acoustic emission test sensor mounting member and an acoustic emission test sensor fixing member; the threaded section is mounted within the connecting screw hole in the lower portion of the base and is fixedly connected via threaded connection; the acoustic emission test sensor mounting member is a cylinder provided with a gap and is fixedly connected with or forms a one-piece structure with the end face of the threaded section, with its inner diameter matching the outer diameter of an acoustic emission test sensor, and the acoustic emission test sensor fixing member consists of a circular elastic plate provided with a gap and a fixing buckle or a fastening screw.
4. The parallelism adjusting member consists of three screws, the parallelism adjusting member mounting mechanism provided at the joint of the main supporting arm and the auxiliary supporting arm consists of two mounting screw holes provided in the main supporting arm and a mounting plate hinged with the main supporting arm and located between the two screw holes, and the mounting plate is provided with a mounting screw hole.

The using method for the universal acoustic emission test sensor fixing device according to the present invention is described as follows:
1. Determine the number of the acoustic emission test sensors and the mounting position thereof at the tested member according to the shape of the tested member and the object of the experiment test, and mount the acoustic emission test sensor within the acoustic emission test sensor fixing device;
2. Place the tested member between upper and lower load press heads of a test machine, respectively, place the acoustic emission test sensors mounted within respective acoustic emission test sensor fixing devices at two sides of different portions of the tested member to be tested respectively, and attach the acoustic emission test sensors to the tested member tightly via the radial positioning mechanism; and
3. Rotate the base so that the end face of the acoustic emission test sensor mounted in the acoustic emission test sensor fixing device is substantially parallel to the coupling surface portion of the tested member, adjust the mounting plate hinged with the main supporting arm to a suitable position, and then adjust the end face of the acoustic emission test sensor via the parallelism adjusting member so that it is substantially parallel to the coupling surface of the tested member.

Upon conformity of mounting and adjusting of the acoustic emission test sensors with requirements, the test piece that needs to be tested can be tested according to a predetermined experiment and test solution.

The present invention realizes the following advantageous effects:
1. As the ball heads of the auxiliary supporting arm form universal revolute pairs with the spherical holes of the bases and the radial positioning mechanism includes elastic members, the universal acoustic emission test sensor fixing device according to the present invention is applicable to tested members of various shapes (being regular or irregular), and the acoustic emission test sensor fixing device can attach the acoustic emission test sensors tightly to the tested member during the whole test process and keep the end face of the acoustic emission test sensors mounted in the acoustic emission test sensor fixing device parallel to the coupling surface of the tested member, thereby ensuring the truthfulness of the test result and improving the accuracy of the test result.
2. As the radial positioning mechanism comprises elastic members, when the tested member swells radially in the test, force of the acoustic emission test sensor will not be increased, which could easily ensure force consistency of the acoustic emission test sensor during testing for the same batch of tested members, thereby lowering the influence of the pseudo signals on the testing result and also improving the life of the acoustic emission testing sensor.
3. The acoustic emission test sensor fixing device according to the present invention makes it convenient to arrange the acoustic emission test sensor at any position on the surface of the tested member, and other deforming test sensors can be arranged at the same time, so as to obtain more different testing information of the tested member during the same testing process.
4. Using the acoustic emission test sensor fixing device according to the present invention, the acoustic emission test sensor can be mounted at any period of time before or after pre-adding contact load to the tested member, and the position of the acoustic emission test sensor can also be adjusted during the experiment.
5. The universal acoustic emission test sensor fixing device according to the present invention is convenient in use, it can be mounted quickly, and can improve test efficiency.

In the figures: 1-screw, 2-rigid end, 3-arc elastomer, 4-main supporting arm, 5-parallelism adjusting member, 6-parallelism adjusting member mounting plate, 7-auxiliary supporting arm, 8-base, 9-acoustic emission test sensor mounting mechanism, 10-acoustic emission test sensor, 11-tested member, 12-semicircular elastomer, 13-mounting screw hole in the parallelism adjusting member, 14-ball head, 15-slot, 16-plugboard, 17-cylinder provided with gap, 18-circular elastic plate provided with gap, 19-sensor fixing buckle, 20-plugboard fixing buckle, 21-plugboard fixing screw hole, 22-sensor fastening screw, 23-connecting screw hole, and 24-threaded section.

DETAILED DESCRIPTION OF THE INVENTION

The specific structure of the universal acoustic emission test sensor fixing device according to the present invention will be further detailed hereinafter in conjunction with the accompanying drawings.

Embodiment 1

Figure 1:
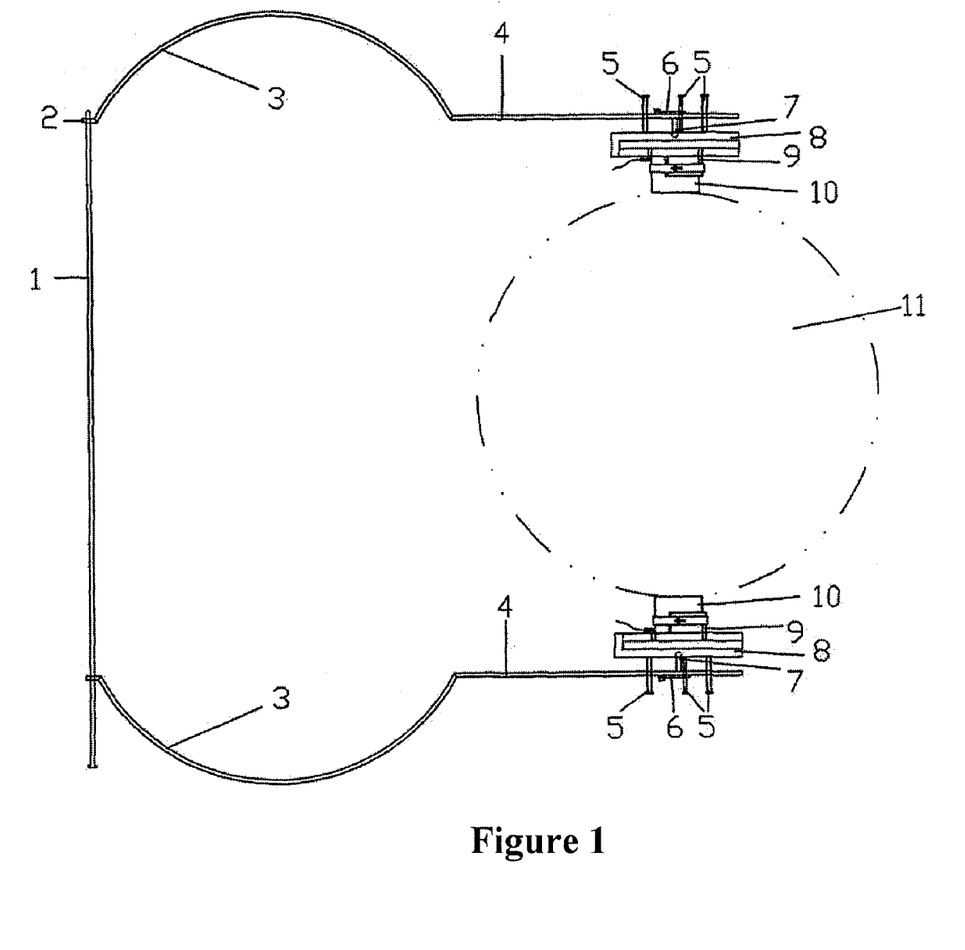
FIG. 1 is a schematic view illustrating a first structure of the universal acoustic emission test sensor fixing device according to the present invention.

In this embodiment, the structure of the universal acoustic emission test sensor fixing device is shown in FIG. 1, comprising a radial positioning mechanism, supporting mechanisms, bases 8, acoustic emission test sensor mounting mechanisms 9, and parallelism adjusting members 5, wherein the supporting mechanisms, the bases, the acoustic emission test sensor mounting mechanisms, and the parallelism adjusting members are all in two sets.

Figure 4:
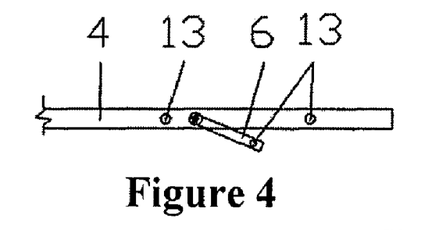
FIG. 4 is a schematic view illustrating the parallelism adjusting member mounting mechanism provided on the main supporting arm in the universal acoustic emission test sensor fixing device according to the present invention.
Figure 5:
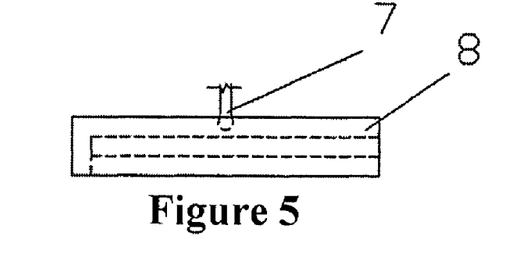
FIG. 5 is a schematic view illustrating a structure of the base in the universal acoustic emission test sensor fixing device according to the present invention and an assembling of the base and the auxiliary supporting arm.
Figure 6:
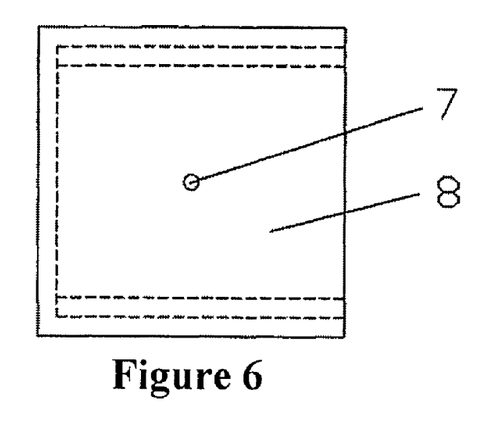
FIG. 6 is a top view of FIG. 5.
Figure 7:
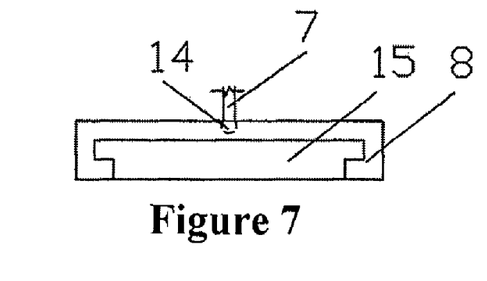
FIG. 7 is a right view of FIG. 5.
Figure 8:
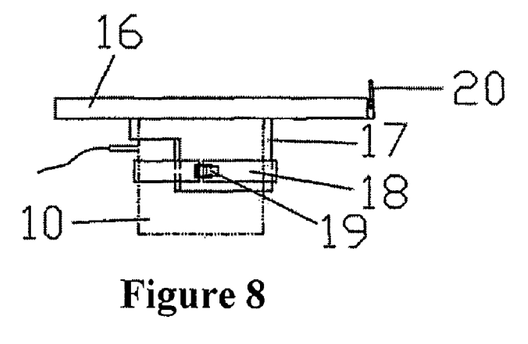
FIG. 8 is a schematic view illustrating a first structure of the acoustic emission test sensor mounting mechanism in the universal acoustic emission test sensor fixing device according to the present invention.
Figure 9:
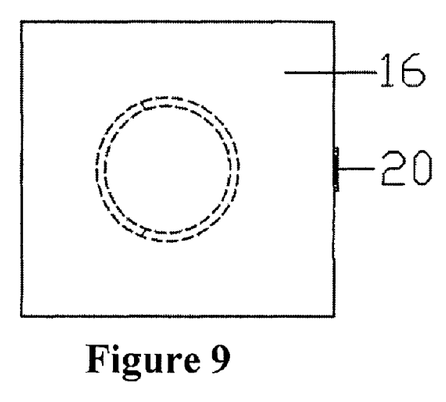
FIG. 9 is a top view of FIG. 8.

The radial positioning mechanism, as shown in FIG. 1, comprises two arc elastomers 3 and one screw 1, and the two arc elastomers are respectively connected with rigid ends 2 at respective one end, each of said rigid ends is provided with a screw hole matching the screw, and the screw forms screw pairs respectively with the screw holes in the two rigid ends. The supporting mechanism, as shown in FIG. 1, comprises a main supporting arm 4 and an auxiliary supporting arm 7; the main supporting arm 4 is made of nickel titanium alloy and has a rectangular cross section; a parallelism adjusting member mounting mechanism is provided at the joint of the main supporting arm and the auxiliary supporting arm, as shown in FIG. 4, the parallelism adjusting member mounting mechanism consists of two mounting screw holes 13 provided in the main supporting arm and a mounting plate 6 hinged with the main supporting arm and located between the two screw holes, and the mounting plate 6 provided with one mounting screw hole 13 therein; the auxiliary supporting arm 7 is made of nickel titanium alloy and has a circular cross section, with its one end fixed on the main supporting arm via threaded connection and the other end provided with ball heads 14 (as shown in FIGS. 1 and 7). The base 8, as shown in FIGS. 5, 6 and 7, has an overall shape of rectangular platform, and the base is provided with a slot 15 in the lower portion, and the spherical hole matching the ball head of the auxiliary supporting arm is provided in the upper surface of the base. The acoustic emission test sensor mounting mechanism 9, as shown in FIGS. 8 and 9, comprises a plugboard 16 matching the slot in the base, a cylinder 17 with a gap, a circular elastic plate 18 with a gap and a fixing buckle 19, wherein the plugboard 16 is provided with a plugboard fixing buckle 20, the cylinder 17 is fixedly connected with the plugboard 16 at the end without the gap, and the end thereof with the gap is a free end, the circular elastic plate 18 provided with the gap is put around the gap section of the cylinder, and the acoustic emission test sensor 10 is fixed within the cylinder 17 via the fixing buckle 19. The parallelism adjusting member 5 consists of three screws.

The above assemblies and members are assembled as follows: the main supporting arms 4 of the two sets of supporting mechanisms are respectively connected to the two free ends of the two arc elastomers 3 of the radial positioning mechanism, in the way that the two auxiliary supporting arms 7 are respectively located at the inner sides of the main supporting arms and are arranged axis symmetrically with respect to the central line of the radial positioning mechanism; the ball heads 14 of the two auxiliary supporting arms are respectively located in the spherical holes in the two bases to form universal revolute pairs; the plugboards 16 of the two sets of acoustic emission test sensor mounting mechanisms are respectively inserted into the slots 15 of the two bases and are fixed via the plugboard fixing buckles 20; and the screws making up of the two sets of parallelism adjusting members 5 are respectively mounted in the screw holes 13 in the parallelism adjusting member mounting mechanism provided on the two main supporting arms 4.

Embodiment 2

Figure 2:
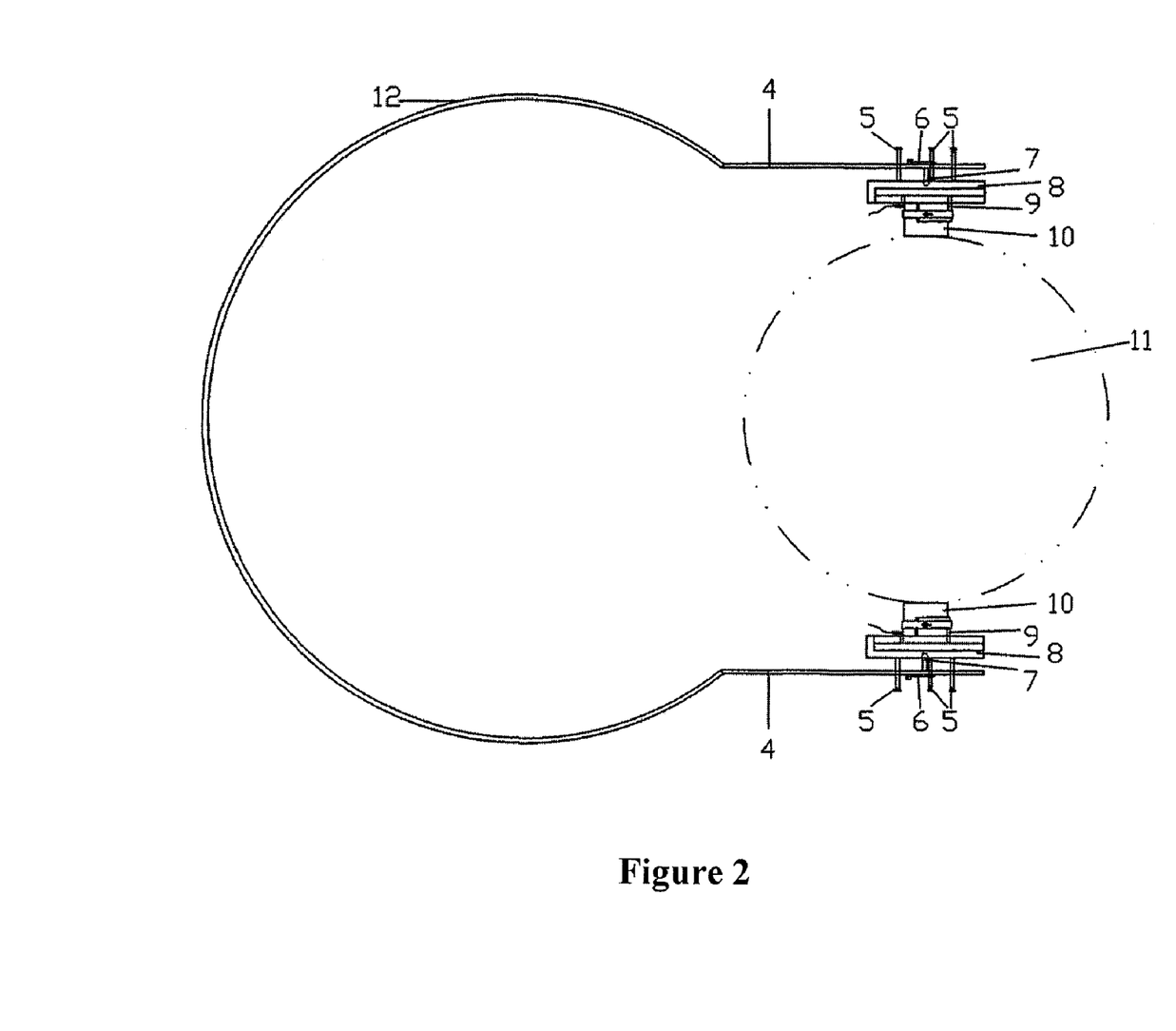
FIG. 2 is a schematic view illustrating a second structure of the universal acoustic emission test sensor fixing device according to the present invention.

In this embodiment, the structure of the universal acoustic emission test sensor fixing device is shown in FIG. 2, comprising a radial positioning mechanism, supporting mechanisms, bases 8, acoustic emission test sensor mounting mechanisms 9, and parallelism adjusting members 5, wherein the supporting mechanisms, the bases, the acoustic emission test sensor mounting mechanisms, and the parallelism adjusting members are all in two sets.

Figure 12:
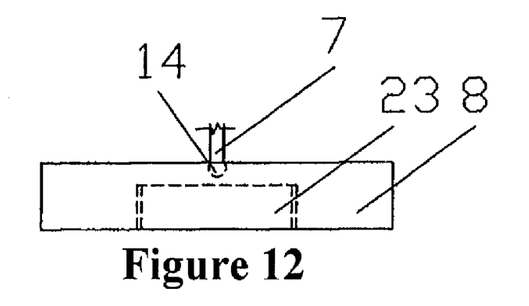
FIG. 12 is a schematic view illustrating another structure of the base in the universal acoustic emission test sensor fixing device according to the present invention and an assembling of the base and the auxiliary supporting arm.
Figure 13:
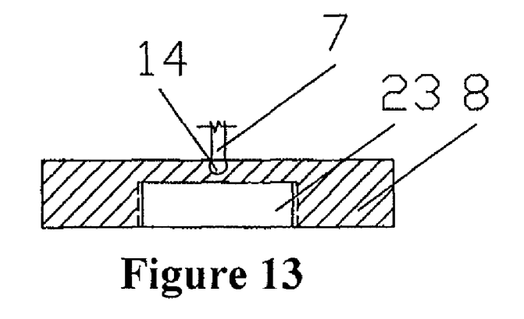
FIG. 13 is a top view of FIG. 12.
Figure 14:
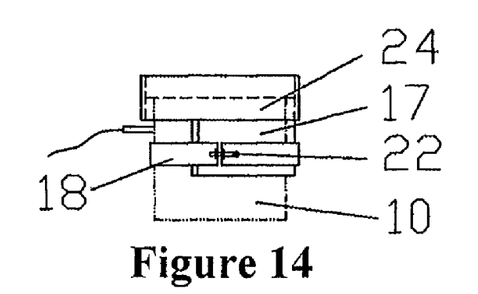
FIG. 14 is a schematic view illustrating a third structure of the acoustic emission test sensor mounting mechanism in the universal acoustic emission test sensor fixing device according to the present invention.
Figure 15:
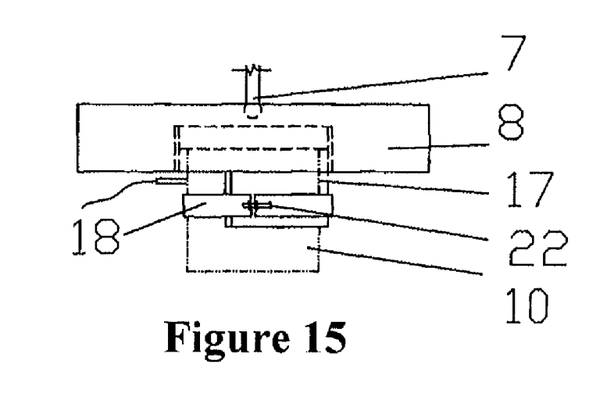
FIG. 15 is a schematic view illustrating the assembling of the base in FIG. 12 and the acoustic emission test sensor mounting mechanism in FIG. 14.

Different from embodiment 1, it is described in embodiment 2 that: 1) the radial positioning mechanism is a semicircular elastomer 12 (as shown in FIG. 2); and 2) the base 8, as shown in FIGS. 12 and 13, is provided with a connecting screw hole 23 in the lower portion; the acoustic emission test sensor mounting mechanism 9, as shown in FIG. 14, comprises a threaded section 24 matching the connecting screw hole in the base, a cylinder 17 provided with a gap, a circular elastic plate 18 provided with a gap, and a fastening screw 22, wherein the threaded section 24 is mounted within the connecting screw hole 23 in the lower portion of the base and is fixedly connected with the base 8 via threaded connection (as shown in FIG. 15), the cylinder 17 provided with a gap and the threaded section 24 form a one-piece structure, and the end of the cylinder with the gap is a free end; the circular elastic plate 18 provided with a gap is put around the gap section of the cylinder, and the acoustic emission test sensor 10 is fixed within the cylinder 17 via the fastening screw 22.

Embodiment 3

Figure 3:
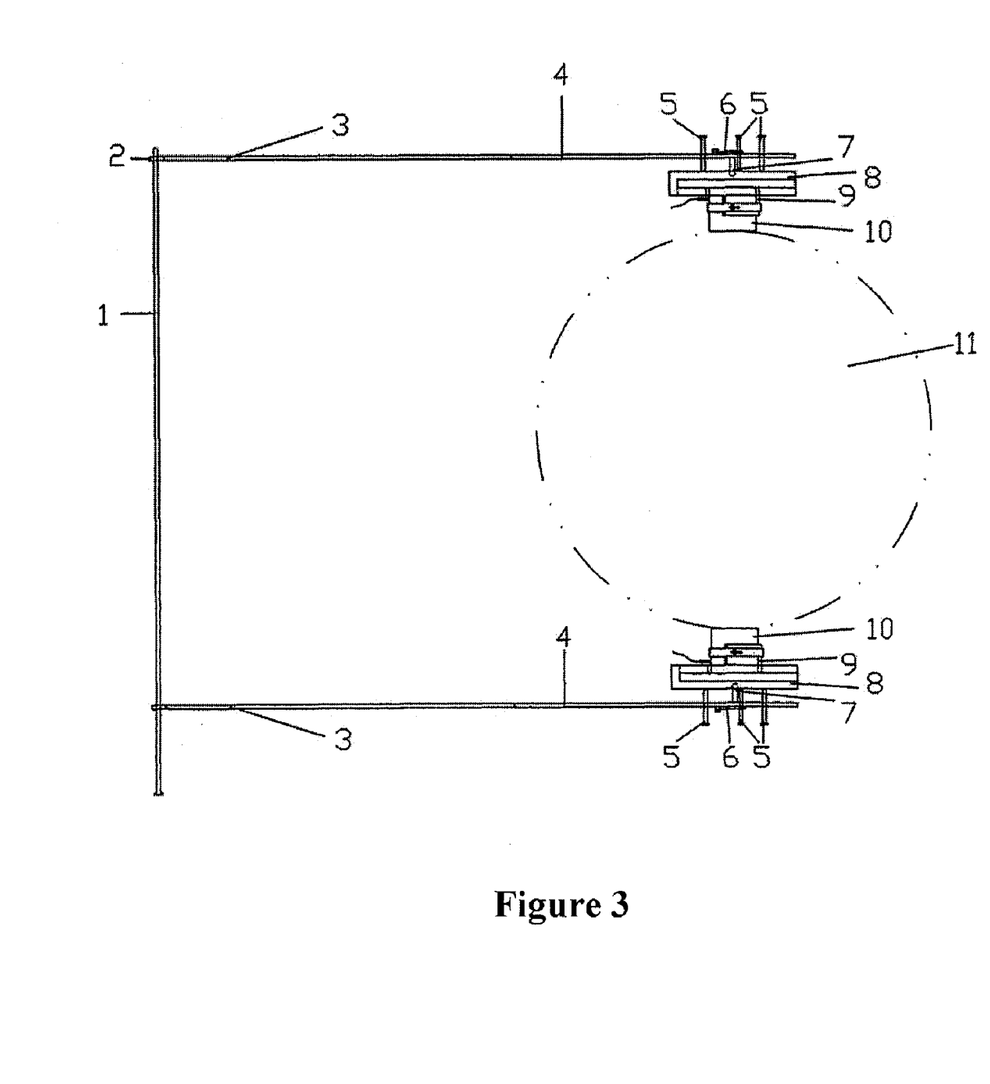
FIG. 3 is a schematic view illustrating a third structure of the universal acoustic emission test sensor fixing device according to the present invention.

In this embodiment, the structure of the universal acoustic emission test sensor fixing device is shown in FIG. 3, comprising a radial positioning mechanism, supporting mechanisms, bases 8, acoustic emission test sensor mounting mechanisms 9, and parallelism adjusting members 5, wherein the supporting mechanisms, the bases, the acoustic emission test sensor mounting mechanisms, and the parallelism adjusting members are all in two sets.

Figure 10:
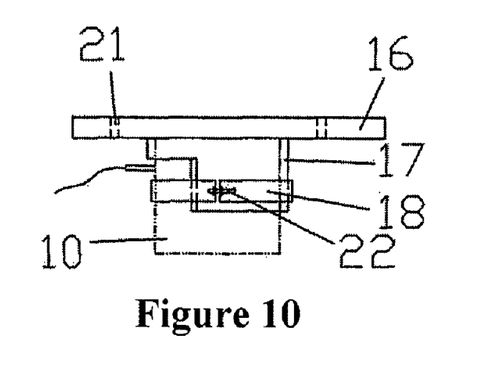
FIG. 10 is a schematic view illustrating a second structure of the acoustic emission test sensor mounting mechanism in the universal acoustic emission test sensor fixing device according to the present invention.
Figure 11:
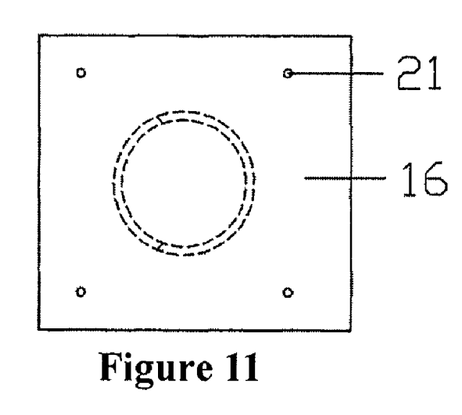
FIG. 11 is a top view of FIG. 10.

Different from embodiment 1, it is described in embodiment 3 that: 1) the radial positioning mechanism, as shown in FIG. 3, comprises a straight-bar elastomer 3 and a screw 1, and the two straight-bar elastomers are respectively connected with rigid ends 2 at respective one end, with the rigid end is provided therein with a screw hole matching the screw, and the screw forms a screw pair with the screw holes in the two rigid ends; 2) the auxiliary supporting arm 7 is hinged with the main supporting arm 4; and 3) the acoustic emission test sensor mounting mechanism 9, as shown in FIGS. 10 and 11, comprises a plugboard 16 matching the slot in the base, a cylinder 17 provided with a gap, a circular elastic plate 18 provided with a gap, and a fastening screw 22, wherein the plugboard 16 is provided with four plugboard fixing screw holes 21 therein, and is fixed within the slot 15 in the base via a bolt, the cylinder 17 and the plugboard 16 form a one-piece structure, and the end of the cylinder with the gap is a free end; the circular elastic plate 18 provided with a gap is put around the gap section of the cylinder, and the acoustic emission test sensor 10 is fixed within the cylinder 17 via the fastening screw 22.

What is claimed is:

1. A universal acoustic emission test sensor fixing device, comprising:
    a radial positioning mechanism, supporting mechanisms, bases, acoustic emission test sensor mounting mechanisms, and parallelism adjusting members, wherein the supporting mechanism, the bases, the acoustic emission test sensor mounting mechanisms, and the parallelism adjusting members are all in two sets;
    the supporting mechanism includes a main supporting arm and an auxiliary supporting arm, with one end of the auxiliary supporting arm fixedly connected to or hinged with the main supporting arm and the other end being provided with a ball head, and a parallelism adjusting member mounting mechanism is provided at the joint of the main supporting arm and the auxiliary supporting arm, and the bases are provided with a spherical hole therein matching the ball head of the auxiliary supporting arm; and
    the main supporting arms of the two sets of supporting mechanisms are respectively connected to the two free ends of the radial positioning mechanism in the way that the auxiliary supporting arms of the two sets of supporting mechanisms are respectively located at the inner sides of the main supporting arms and are arranged axis symmetrically with respect to the central line of the radial positioning mechanism, and the ball heads of the two auxiliary supporting arms are respectively located within the spherical holes of the two bases to form a universal revolute pairs, the two sets of acoustic emission test sensor mounting mechanisms are respectively mounted at the two bases, and the two sets of parallelism adjusting members are respectively mounted on the two main supporting arms via mounting mechanisms provided on the main supporting arms.

2. The universal acoustic emission test sensor fixing device according to claim 1, wherein the radial positioning mechanism includes two elastomers and one screw, with the two elastomers respectively connected with rigid ends at respective one end, the rigid end is provided with a screw hole matching the screw, and the screw forms a screw pair with the screw holes in the two rigid ends.

3. The universal acoustic emission test sensor fixing device according to claim 1, wherein the radial positioning mechanism consists of an elastomer.

4. The universal acoustic emission test sensor fixing device according to claim 1, wherein the bases are provided with slots in the lower portion, and the spherical holes matching the ball heads of the auxiliary supporting arm are provided in the upper surface of the bases; and
    the acoustic emission test sensor mounting mechanism comprises plugboards matching the slots in the bases, an acoustic emission test sensor mounting member and an acoustic emission test sensor fixing member, wherein the plugboards are provided with plugboard fixing buckles or a plugboard fixing screw hole, the acoustic emission test sensor mounting member is a cylinder provided with a gap and is fixedly connected with or forms a one-piece structure with the plugboards, with its inner diameter matching the outer diameter of an acoustic emission test sensor, and the acoustic emission test sensor fixing member consists of a circular elastic plate provided with a gap and a fastening screw or a fixing buckle.

5. The universal acoustic emission test sensor fixing device according to claim 1, wherein the bases are provided with a connecting screw holes in the lower portion, and the spherical holes matching the ball heads of the auxiliary supporting arm are provided in the upper surface of the bases; and
    the acoustic emission test sensor mounting mechanism includes threaded sections matching the connecting screw holes in the bases, an acoustic emission test sensor mounting member and an acoustic emission test sensor fixing member, wherein the acoustic emission test sensor mounting member is a cylinder provided with a gap and is fixedly connected with or forms a one-piece structure with the threaded sections, with its inner diameter matching the outer diameter of an acoustic emission test sensor, and the acoustic emission test sensor fixing member consists of a circular elastic plate provided with a gap and a fastening screw or a fixing buckle.

6. The universal acoustic emission test sensor fixing device according to claim 1, wherein each of the parallelism adjusting members consists of three screws, the parallelism adjusting member mounting mechanism provided at the joint of the main supporting arm and the auxiliary supporting arm consists of two mounting screw holes provided in the main supporting arm and a mounting plate hinged with the main supporting arm and located between the two screw holes, and the mounting plate are provided with mounting screw holes.

7. The universal acoustic emission test sensor fixing device according to claim 4, wherein the parallelism adjusting member consists of three screws, the parallelism adjusting member mounting mechanism provided at the joint of the main supporting arm and the auxiliary supporting arm consists of two mounting screw holes provided in the main supporting arm and a mounting plate hinged with the main supporting arm and located between the two screw holes, and the mounting plate is provided with a mounting screw hole therein.

8. The universal acoustic emission test sensor fixing device according to claim 5, wherein each of the parallelism adjusting member consists of three screws, the parallelism adjusting member mounting mechanism provided at the joint of the main supporting arm and the auxiliary supporting arm consists of two mounting screw holes provided in the main supporting arm and mounting plates hinged with the main supporting arm and located between the two screw holes, and each of the mounting plates is provided with a mounting screw hole therein.

9. The universal acoustic emission test sensor fixing device according to claim 2, wherein the bases are provided with slots in the lower portion, and the spherical holes matching the ball heads of the auxiliary supporting arm are provided in the upper surface of the bases; and the acoustic emission test sensor mounting mechanism comprises plugboards matching the slots in the bases, an acoustic emission test sensor mounting member and an acoustic emission test sensor fixing member, wherein the plugboards are provided with plugboard fixing buckles or a plugboard fixing screw hole, the acoustic emission test sensor mounting member is a cylinder provided with a gap and is fixedly connected with or forms a one-piece structure with the plugboards, with its inner diameter matching the outer diameter of an acoustic emission test sensor, and the acoustic emission test sensor fixing member consists of a circular elastic plate provided with a gap and a fastening screw or a fixing buckle.

10. The universal acoustic emission test sensor fixing device according to claim 3, wherein the bases are provided with slots in the lower portion, and the spherical holes matching the ball heads of the auxiliary supporting arm are provided in the upper surface of the bases; and the acoustic emission test sensor mounting mechanism comprises plugboards matching the slots in the bases, an acoustic emission test sensor mounting member and an acoustic emission test sensor fixing member, wherein the plugboards are provided with plugboard fixing buckles or a plugboard fixing screw hole, the acoustic emission test sensor mounting member is a cylinder provided with a gap and is fixedly connected with or forms a one-piece structure with the plugboards, with its inner diameter matching the outer diameter of an acoustic emission test sensor, and the acoustic emission test sensor fixing member consists of a circular elastic plate provided with a gap and a fastening screw or a fixing buckle.

11. The universal acoustic emission test sensor fixing device according to claim 2, wherein the bases are provided with a connecting screw holes in the lower portion, and the spherical holes matching the ball heads of the auxiliary supporting arm are provided in the upper surface of the bases; and the acoustic emission test sensor mounting mechanism includes threaded sections matching the connecting screw holes in the bases, an acoustic emission test sensor mounting member and an acoustic emission test sensor fixing member, wherein the acoustic emission test sensor mounting member is a cylinder provided with a gap and is fixedly connected with or forms a one-piece structure with the threaded sections, with its inner diameter matching the outer diameter of an acoustic emission test sensor, and the acoustic emission test sensor fixing member consists of a circular elastic plate provided with a gap and a fastening screw or a fixing buckle.

12. The universal acoustic emission test sensor fixing device according to claim 3, wherein the bases are provided with a connecting screw holes in the lower portion, and the spherical holes matching the ball heads of the auxiliary supporting arm are provided in the upper surface of the bases; and the acoustic emission test sensor mounting mechanism includes threaded sections matching the connecting screw holes in the bases, an acoustic emission test sensor mounting member and an acoustic emission test sensor fixing member, wherein the acoustic emission test sensor mounting member is a cylinder provided with a gap and is fixedly connected with or forms a one-piece structure with the threaded sections, with its inner diameter matching the outer diameter of an acoustic emission test sensor, and the acoustic emission test sensor fixing member consists of a circular elastic plate provided with a gap and a fastening screw or a fixing buckle.

13. The universal acoustic emission test sensor fixing device according to claim 2, wherein each of the parallelism adjusting members consists of three screws, the parallelism adjusting member mounting mechanism provided at the joint of the main supporting arm and the auxiliary supporting arm consists of two mounting screw holes provided in the main supporting arm and a mounting plate hinged with the main supporting arm and located between the two screw holes, and the mounting plate are provided with mounting screw holes.

14. The universal acoustic emission test sensor fixing device according to claim 3, wherein each of the parallelism adjusting members consists of three screws, the parallelism adjusting member mounting mechanism provided at the joint of the main supporting arm and the auxiliary supporting arm consists of two mounting screw holes provided in the main supporting arm and a mounting plate hinged with the main supporting arm and located between the two screw holes, and the mounting plate are provided with mounting screw holes.

* * * * *